United States Patent [19] [11] 4,052,191
Krenzer [45] Oct. 4, 1977

[54] 1-THIADIAZOLYL-5-ALKYL- AND ARYLAMINOIMIDAZOLIDINONES

[75] Inventor: John Krenzer, Oak Park, Ill.

[73] Assignee: Velsicol Chemical Corporation, Chicago, Ill.

[21] Appl. No.: 666,285

[22] Filed: Mar. 12, 1976

[51] Int. Cl.² ............ A01N 9/12; C07D 285/12
[52] U.S. Cl. ............................ 71/90; 260/306.8 D
[58] Field of Search ............... 71/90; 260/306.8 D

[56] References Cited
U.S. PATENT DOCUMENTS

| | | | |
|---|---|---|---|
| 3,758,492 | 9/1973 | Metzger et al. | 71/90 |
| 3,759,939 | 9/1973 | Metzger et al. | 71/90 |
| 3,773,780 | 11/1973 | Metzger et al. | 71/90 |
| 3,849,432 | 11/1974 | Metzger et al. | 71/90 |

Primary Examiner—Lewis Gotts
Assistant Examiner—Catherine L. Mills
Attorney, Agent, or Firm—Robert J. Schwarz; Dietmar H. Olesch

[57] ABSTRACT

This invention discloses new compounds of the formula

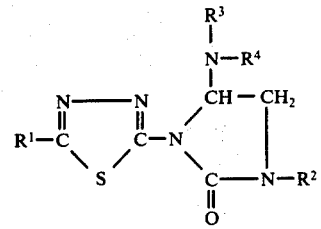

wherein $R^1$ is selected from the group consisting of alkyl, cycloalkyl, alkenyl, haloalkyl, alkoxy, alkylthio, alkylsulfonyl and alkylsulfinyl; $R^2$ is selected from the group consisting of alkyl, alkenyl, haloalkyl and

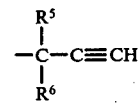

wherein $R^5$ and $R^6$ are each selected from the group consisting of hydrogen and alkyl; and $R^3$ and $R^4$ are each selected from the group consisting of hydrogen, alkyl of up to 18 carbon atoms, alkenyl, haloalkyl, hydroxyalkyl, alkoxyalkyl, cycloalkyl and

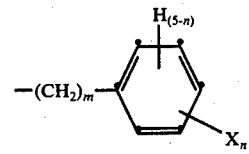

wherein X is selected from the group consisting of alkyl, alkoxy, halogen, haloalkyl, alkylthio, nitro and cyano; $n$ is an integer from 0 to 3; and $m$ is the integer 0 or 1, provided that a maximum of one of $R^3$ and $R^4$ is an aromatic moiety. Further disclosed is the herbicidal utility of the foregoing compounds.

10 Claims, No Drawings

1-THIADIAZOLYL-5-ALKYL- AND ARYLAMINOIMIDAZOLIDINONES

This invention relates to new compositions of matter and more specifically relates to new chemical compounds of the formula

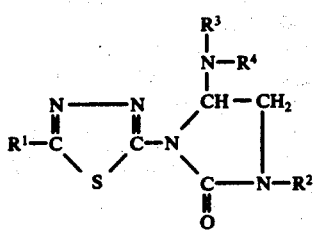
(I)

wherein $R^1$ is selected from the group consisting of alkyl, cycloalkyl, alkenyl, haloalkyl, alkoxy, alkylthio, alkylsulfonyl and alkylsulfinyl; $R^2$ is selected from the group consisting of alkyl, alkenyl, haloalkyl and

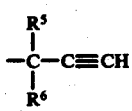

wherein $R^5$ and $R^6$ are each selected from the group consisting of hydrogen and alkyl; and $R^3$ and $R^4$ are each selected from the group consisting of hydrogen, alkyl of up to 18 carbon atoms, alkenyl, haloalkyl, hydroxyalkyl, alkoxyalkyl, cycloalkyl and

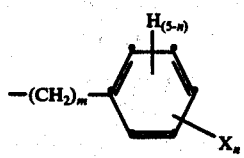

wherein X is selected from the group consisting of alkyl, alkoxy, halogen, haloalkyl, alkylthio, nitro and cyano; n is an integer from 0 to 3; and m is the integer 0 or 1, provided that a maximum of one of $R^3$ and $R^4$ is an aromatic moiety.

The compounds of the present invention are unexpectedly useful as herbicides.

In a preferred embodiment of this invention $R^1$ is selected from the group consisting of alkyl of up to 18 carbon atoms, cycloalkyl of from 3 to 7 carbon atoms, lower alkenyl, lower chloroalkyl, lower bromoalkyl, trifluoromethyl, lower alkoxy, lower alkylthio, lower alkylsulfonyl and lower alkylsulfinyl; $R^2$ is selected from the group consisting of lower alkyl, lower alkenyl, lower haloalkyl and propargyl; and $R^3$ and $R^4$ are each selected from the group consisting of hydrogen, lower alkyl, lower alkenyl, lower haloalkyl, lower hydroxyalkyl, lower alkoxyalkyl, cycloalkyl of from 3 to 7 carbon atoms and

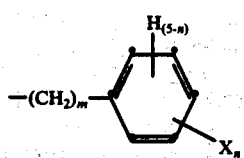

wherein X is selected from the group consisting of lower alkyl, lower alkoxy, halogen, lower haloalkyl, nitro, cyano and lower alkylthio; n is a integer from 0 to 3; and m is the integer 0 or 1, provided that a maximum of one of $R^3$ and $R^4$ is an aromatic moiety.

The term "lower" as used herein designates a straight or branched carbon chains of up to six carbon atoms.

The compounds of the present invention can be prepared by reacting a compond of the formula

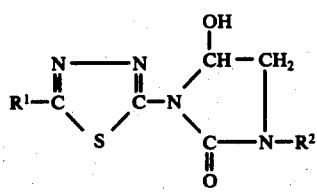
(II)

wherein $R^1$ and $R^2$ are as heretofore described, with an amine of the formula

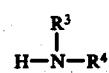
(III)

wherein $R^3$ and $R^4$ are as heretofore described. This reaction can be effected by combining the compound of formula II with an about equimolar amount or excess molar amount of the amine of formula III in an inert organic reaction medium, such as heptane or toluene, and then heating the reaction mixture, with stirring, at its reflux temperature and azeotropically removing the water of reaction. After this time the reaction mixture can be cooled, and the desired product can be recovered by filtration if formed as a precipitate or upon evaporation of the organic reaction medium if soluble therein. The product can then be purified by conventional means such as recrystallization and the like.

The compounds of formula II can be readily prepared by heating a compound of the formula

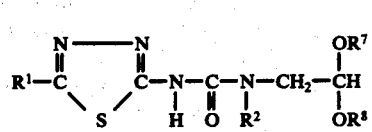
(IV)

wherein $R^1$ and $R^2$ are as heretofore described and $R^7$ and $R^8$ are methyl or ethyl, in a dilute, aqueous, acidic reaction medium for a period of about 10 to about 60 minutes. Temperatures of from about 70° C to the reflux temperature of the reaction mixture can be utilized. The reaction medium can comprise a dilute, aqueous inorganic acid such as hydrochloric acid at a concentration of from about 0.5 to about 5 percent. Upon completion of the reaction the desired product can be recovered as a precipitate by cooling the reaction mixture. This product can be used as such or can be further purified by conventional means such as recrystallization and the like.

The compounds of formula IV can be prepared by reacting a molar amount of an isocyanate dimer of the formula (V)

-continued

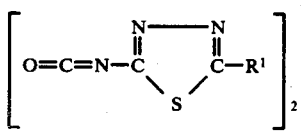

wherein R¹ is as heretofore described, with about two molar amounts of a dimethyl acetal of the formula

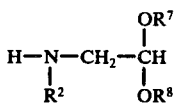

(VI)

wherein R², R⁷ and R⁸ are as heretofore described. This reaction can be effected by heating a mixture of the isocyanate dimer and the acetal in an inert organic reaction medium such as benzene at the reflux temperature of the reaction mixture. Heating at reflux can be continued for a period of from about 2 to about 30 minutes to ensure completion of the reaction. After this time the desired product can be recovered upon evaporation of the reaction medium and can be used as such or can be further purified by standard techniques in the art.

The isocyanate dimer of formula V can be prepared by reacting a thiadiazole of the formula

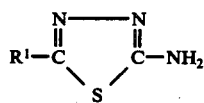

(VII)

wherein R¹ is as heretofore described, with phosgene. This reaction can be effected by adding a slurry or solution of the thiadiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration, if formed as a precipitate, or upon evaporation of the organic solvent used if soluble therein. This product can be used as such or can be further purified as desired.

Exemplary thiadiazoles of formula VII useful for preparing the compounds of the present invention are 5-methyl-2-amino-1,3,4-thiadiazole, 5-ethyl-2-amino-1,3,4-thiadiazole, 5-propyl-2-amino-1,3,4-thiadiazole, 5-t-butyl-2-amino-1,3,4-thiadiazole, 5-allyl-2-amino-1,3,4-thiadiazole, 5-pent-3-enyl-2-amino-1,3,4-thiadiazole, 5-β-chloroethyl-2-amino-1,3,4-thiadiazole, 5-γ-chloropropyl-2-amino-1,3,4-thiadiazole, 5-trifluorometyl-2-amino-1,3,4-thiadiazole, 5-methoxy-2-amino-1,3,4-thiadiazole, 5-ethoxy-2-amino-1,3,4-thiadiazole, 5-propoxy-2-amino-1,3,4-thiadiazole, 5-butyloxy-2-amino-1,3,4-thiadiazole, 5-hexyloxy-2-amino-1,3,4-thiadiazole, 5-methylthio-2-amino-1,3,4-thiadizole, 5-ethylthio-2-amino-1,3,4-thiadiazole, 5-propylthio-2-amino-1,3,4-thiadiazole, 5-butylthio-2-amino-1,3,4-thiadiazole, 5-methylsulfonyl-2-amino-1,3,4-thiadiazole, 5-ethylsulfonyl-2-amino-1,3,4-thiadiazole, 5-butylsulfonyl-2-amino-1,3,4-thiadiazole, 5-methylsulfinyl-2-amino-1,3,4-thiadiazole, 5-ethylsulfinyl-2-amino-1,3,4-thiadiazole, 5-propylsulfinyl-2-amino-1,3,4-thiadiazole, 5-butylsulfinyl-2-amino-1,3,4-thiadiazole and the like.

Exemplary suitable acetals of formula VI for preparing the compounds of this invention are the dimethyl acetal of 2-methylaminoacetaldehyde, the dimethyl acetal of 2-ethylaminoacetaldehyde, the dimethyl acetal of 2-propylaminoacetaldehyde, the dimethyl acetal of 2-butylaminoacetaldehyde, the dimethyl acetal of 2-pentylaminoacetaldehyde and the dimethyl acetal of 2-hexylaminoacetaldehyde.

Exemplary suitable amines of formula III are methylamine, ethylamine, propylamine, butylamine, isopropylamine, sec-butylamine, t-butylamine, pentylamine, hexylamine, heptylamine, octylamine, decylamine, dodecylamine, hexadecylamine, octadecylamine, dioctylamine, didodecylamine, dioctadecylamine, dimethylamine, diethylamine, dipropylamine, dibutylamine, dihexylamine, N-methyl-N-ethylamine, N-ethyl-N-hexylamine, cyclopropylamine, cyclobutylamine, cyclopentylamine, cyclohexylamine, cycloheptylamine β-chloroethylamine, γ-bromopropylamine, δ-chlorobutylamine, δ,δ-dichlorobutylamine, allylamine, but-3-enylamine, pent-4-enylamine, hex-4-enylamine, methoxymethylamine, methoxyethylamine, ethoxymethylamine, methoxypropylamine, ethoxpropylamine, phenylamine, 3-chlorophenylamine, 4-bromophenylamine, 2-methoxyphenylamine, 4-trifluoromethylphenylamine, 3-methylthiophenylamine, 4-nitrophenylamine, 4-cyanophenylamine, 3,4-dichlorobenzylamine, 2-methyl-4-chlorobenzylamine, 3,4,5-trichlorophenylamine, N-methyl-N-(3,4-dibromophenyl)amine and the like.

The manner in which the compounds of the present invention can be prepared is more specifically illustrated in the following examples.

EXAMPLE 1

Preparation of 5-Trifluoromethyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-trifluoromethyl-2-amino-1,3,4-thiadiazole (45 grams) in ethyl acetate (300 ml) was added to the reaction vessel, and the resulting mixture was stirred for a period of about 16 hours resulting in the formation of precipitate. The reaction mixture was then purged with nitrogen gas to remove unreacted phosgene. The purged mixture was filtered to recover 48 grams of a white solid. This solid was recrystallized from dimethyl formamide to yield the desired product 5-trifluoromethyl-1,3,4-thiadiazol-2-yl isocyanate dimer.

EXAMPLE 2

Preparation of the Dimethyl Acetal of 2-[1-Methyl-3-(5-trifluoromethyl-1,3,4-thiadiazol-2-yl)ureido]acetaldehyde A mixture of 5-trifluoromethyl-1,3,4-thiadiazol-2-yl isocyanate dimer (9.5 grams), the dimethyl acetal of 2-methylaminoacetaldehyde (5.8 grams) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. This product is recrystallized from heptane to yield the desired product the dimethyl acetal of 2-[1-methyl-3-(5-trifluoromethyl-1,3,4-thiadiazol-2-yl)ureido]acetaldehyde having a melting point of 101° to 102° C.

EXAMPLE 3

Preparation of
1-(5-Trifluoromethyl-1,3,4-thiadiazol-2-yl)-3-methyl-5-hydroxy-1,3-imidazolidin-2-one The dimethyl acetal of 2-[1-methyl-3-(5-trifluoromethyl-1,3,4-thiadiazol-2-yl)ureido]acetaldehyde (15 grams), water (400 ml) and hydrochloric acid (4 ml) were charged into a glass reaction vessel equipped with a mechanical stirrer, thermometer and reflux condenser. The reaction mixture was heated at reflux for a period of about 15 minutes. The reaction mixture was then filtered while hot and the filtrate was cooled, resulting in the formation of a precipitate. The precipitate was recovered by filtration, was dried and was recrystallized from an ethyl acetate-hexane mixture to yield the desired product 1(5-trifluoromethyl-1,3,4-thiadiazol-2-yl)-3-methyl-5-hydroxy-1,3-imidazolidin-2-one having a melting point of 136° to 138° C.

EXAMPLE 4

Preparation of
1-(5-Trifluoromethyl-1,3,4-thiadiazol-2-yl)-3-methyl-5-t-butylamino-1,3-imidazolidin-2-one 1-(5-Trifluoromethyl-1,3,4-thiadiazol-2-yl)-3-methyl-5-hydroxy-1,3-imidazolidin-2-one (13.1 grams) and heptane (100 ml) were charged into a glass reaction vessel equipped with a mechanical stirrer, thermometer, Dean-Stark trap and reflux condenser. t-Butylamine (7.0 grams) was added to the reaction vessel, and the mixture was heated at reflux while removing the water as it was formed. After no more water was given off, the reaction mixture was cooled, resulting in the precipitation of a crystalline solid. The solid was recovered by filtration and was recrystallized from heptane to yield the desired product 1-(5-trifluoromethyl-1,3,4-thiadiazol-2-yl)-3-methyl-5-t-butylamino-1,3-imidazolidin-2-one having a melting point of 113° to 115° C.

EXAMPLE 5

Preparation of 5-t-Butyl-1,3,4-thiadiazol-2-yl
Isocyanate Dimer

A saturated solution off phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel, and the resulting mixture was stirred for a period of about 16 hours resulting in the formation of a precipitate. The reaction mixture was then purged with nitrogen gas to remove unreacted phosgene. The purged mixture was then filtered to recover the desired product 5-t-butyl-1,3,4-thiadiazol-2yl isocyanate dimer as a solid having a melting point of 261° to 263° C.

EXAMPLE 6

Preparation of the Dimethyl Acetal of
2-[1-Methyl-3-(5-t-butyl-1,3,4-thiadiazol-2-yl)ureido]-acetaldehyde A mixture of 5-t-butyl-1,3,4-thiadiazol-2-yl isocyanate dimer (6 grams), the dimethyl acetal of 2-methylaminoacetaldehyde (3.9 grams) and benzene (50 ml) were charged into a glass reaction flask equipped with a mechanical stirrer and reflux condenser. The reaction mixture was heated at reflux, with stirring for a period of about 5 minutes. After this time the reaction mixture was stripped of benzene to yield an oil which solidified upon standing. The resulting solid was then recrystallized from pentane to yield the desired product the dimethyl acetal of 2-[1-methyl-3-(5-t-butyl-1,3,4-thiadiazol-2-yl)ureido]acetaldehyde having a melting point of 80° to 82° C.

EXAMPLE 7

Preparation of
1-(5-t-Butyl-1,3,4-thiadiazol-2-yl)-3-methyl-5-hydroxy-1,3-imidazolidin-2-one The dimethyl acetal of 2-[1-methyl-3-(5-t-butyl-1,3,4-thiadiazol-2-yl)ureido]acetaldehyde (16 grams), concentrated hydrochloric acid (10 ml) and water (500 ml) were charged into a glass reaction vessel equipped with a mechanical stirrer, thermometer and reflux condenser. The reaction mixture was heated at reflux for a period of about 15 minutes. The reaction mixture was filtered while hot, and the filtrate was then cooled, resulting in the formation of a precipitate. The pricipitate was recovered by filtration, dried and was recyrstallized from a benzene-hexane mixture to yield the desired product 1-(5-t-butyl-1,3,4-thiadiazol-2-yl)-3-methyl-5-hydroxy-1,3-imidazolidin-2-one having a melting point of 133° to 134° C.

EXAMPLE 8

Preparation of
1-(5-t-Butyl-1,3,4-thiadiazol-2-yl)-3-methyl-5-hexylamino-1,3-imidazolidin-2-one 1-(5-t-Butyl-1,3,4-thiadiazol-2-yl)-3-methyl-5-hydroxy-1,3-imidazolidin-2-one (13.4 grams), hexylamine (6.0 grams) and heptane (100 ml) were charged into a glass reaction vessel equipped with a mechanical stirrer, thermometer, reflux condenser and Dean-Startk trap. The reaction mixture was heated at reflux, and the water of reaction was removed as it was formed by azeotroping. After no more water was given off, the reaction mixture was stripped of solvent to yield an oil as the residue. The oil was subjected to vacuum, whereupon it solidified. The resulting solid was then recrystallized from hexane to yield the desired product 1-(5-t-butyl-1,3,4-thiadiazol-2-yl)-3-methyl-5-hexylamino-1,3-imidazolidin-2-one having a melting point of 62° to 64° C.

EXAMPLE 9

Preparation of
1-(5-Trifluoromethyl-1,3,4-thiadiazol-2-yl)-3-methyl-5-hexylamino-1,3-imidazolidin-2-one 1-(5-Trifluoromethyl-1,3,4-thiadiazol-2-yl)-3-methyl-5-hydroxy-1,3-imidazolidin-2-one (13.4 grams), hexylamine (6.0 grams) and heptane (100 ml) were charged into a glass reaction vessel equipped with a mechanical stirrer, thermometer, reflux condenser and Dean-Stark trap. The reaction mixture was heated at reflux, and the water of reaction was removed as it was formed by azeotroping. After no more water was given off, the reaction mixture was stripped of solvent to yield an oil as the residue. This oil was dissolved in pentane and passed through a florex column. The eluant was stripped of solvent and dried under vacuum to yield the desired product 1-(5-trifluoromethyl-1,3,4-thiadiazol-2-yl)-3-methyl-5-hexylamino-1,3-imidazolidin-2-one.

EXAMPLE 10

Preparation of
1-(5-Trifluoromethyl-1,3,4-thiadiazol-2-yl)-3-methyl-5-anilino-1,3-imidazolidin-2-one 1-(5-Trifluoromethyl-1,3,4-thiadiazol-2-yl)-3-methyl-5-hydroxy-1,3-imidazolidin-2-one (13.4 grams), heptane (100 ml) and aniline (6 ml) were charged into a glass reaction vessel equipped with a mechanical stirrer, thermometer, reflux condenser and Dean-Stark trap. The reaction mixture was heated at reflux for a period of about 8 hours, and the water of reaction was removed as it was formed. After this time the reaction mixture was stripped of solvent leaving a solid residue. This solid was recrystallized from isopropanol to yield the desired product 1-(5-trifluoromethyl-1,3,4-thiadiazol-2-yl)-3-methyl-5-anilino-1,3-imidazolidin-2-one having a melting point of 142° to 144° C.

EXAMPLE 11

Preparation of
1-(5-Trifluoromethyl-1,3,4-thiadiazol-2-yl)-3-methyl-5-benzylamino-1,3-imidazolidin-2-one 1-(5-Trifluoromethyl-1,3,4-thiadiazol-2-yl)-3-methyl-5-hydroxy-1,3-imidazolidin-2-one (8 grams), benzylamine (4.5 grams) and heptane (100 ml) were charged into a glass reaction vessel equipped with a mechanical stirrer, thermometer, reflux condenser and Dean-Stark trap. The reaction mixture was heated at reflux, and the water of reaction removed as it was formed. After no more water was formed, the mixture was cooled, resulting in the formation of a solid product. This solid was recovered by filtration to yield the desired product 1-(5-trifluoromethyl-1,3,4-thiadiazol-2yl)-3-yl)-3-methyl-5-benzylamino-1,3-imidazolidin-2-one having a melt point of 97° to 99° C.

EXAMPLE 12

Preparation of
1-(5-Trifluoromethyl-1,3,4-thiadiazol-2-yl)-3-methyl-5-β-hydroxyethylamino-1,3-imidazolidin-2-one 1-(5-Trifluoromethyl-1,3,4-thiadiazol-2-yl)-3-methyl-5-hydroxy-1,3-imidazolidin-2-one (8grams), β-hydroxyethylamine (5 grams) and benzene (75 ml) were charged into a glass reaction flask equipped with a mechanical stirrer, thermometer, reflux condenser and Dead-Stark trap. The reaction mixture was heated at reflux, and the water of reaction was removed as it was formed. After no more water was given off, the reaction mixture was stripped of solvent to yield an oil. This oil was filtered through celite to yield the desired product 1-(5-trifluoromethyl-1,3,4-thiadiazol-2-yl)-3-methyl-5-β-hydroxyethylamino-1,3-imidazolidin-2-one.

EXAMPLE 13

Preparation of
1-(5-Trifluoromethyl-1,3,4-thiadiazol-2-yl)-3-methyl-5-diethylamino-1,3-imidazolidin-2-one 1-(5-Trifluoromethyl-1,3,4-thiadiazol-2-yl)-3-methyl-5-hydroxy-1,3-imidazolidin-2-one (8 grams), diethylamine (3 grams) and benzene (50 ml) were charged into a glass reaction flask equipped with a mechanical stirrer, thermometer, reflux condenser and Dean-Stark trap. The reaction mixture was then heated at reflux, and the water of reaction was removed as it was formed. After no more water was given off, the reaction mixture was stripped of solvent, leaving an oil. This oil was dissolved in pentane, and the resulting solution was passed through a florex column. The eluant was then stripped of pentane, leaving an oil. This oil was dried under vacuum to yield the desired product 1-(5-trifluoromethyl-1,3,4-thiadiazol-2-yl)-3-methyl-5-diethylamino-1,3-imidazolidin-2-one.

EXAMPLE 14

Preparation of
1-(5-t-Butyl-1,3,4-thiadiazol-2-yl)-3-methyl-5-β-hydroxyethylamino-1,3-imidazolidin-2-one 1-(5-t-Butyl-1,3,4-thiadiazol-2-yl)-3-methyl-5-hydroxy-1,3imidazolidin-2-one (8 grams), β-hydroxyethylamine (3 grams) and benzene (75 ml) were charged into a glass reaction vessel equipped with a mechanical stirrer, thermometer, reflux condenser and Dean-Startk trap. The reaction mixture was heated at reflux, and the water of reaction was removed as it was formed. After no more water evolved, the reaction mixture was stripped of benzene, leaving a solid product. This solid was recrystallized from ethyl acetate to yield the desired product 1-(5-t-butyl-1,3,4-thiadiazol-2-yl)-3-methyl-5-β-hydroxyethylamino-1,3-imidazolidin-2-one having a melt point of 128° to 130° C.

EXAMPLE 15

Preparation of
1-(5-Trifluoromethyl-1,3,4-thiadiazol-2-yl)-3-methyl-5-(2-methoxyisopropylamino)-1,3-imidazolidin-2-one 1-(5-Trifluoromethyl-1,3,4-thiadiazol-2yl)-3-methyl-5-hydroxy-1,3-imidazolidin-2-one (8 grams), 2-methoxyisopropylamine (5 grams) and benzene (70 ml) were charged into a glass reaction vessel equipped with a mechanical stirrer, thermometer, reflux condenser and Dean-Stark trap. The reaction mixture was heated at reflux, and the water of reaction was removed as it was formed. After no more water was given off, the reaction mixture was stripped of solvent, leaving an oil. This oil was filtered through celite to yield the desired product 1-(5-trifluoromethyl-1,3,4-thiadiazol-2-yl)-3-methyl-5-(2-methoxyisopropylamino)-1,3-imidazolidin-2one.

EXAMPLE 16

Preparation of 5-Hexyl-1,3,4-thiadiazol-2-yl Isocyanate Dimer

A saturated solution of phosgene in ethyl acetate (100 ml) is charged into a glass reaction vessel equipped with a mechanical stirred. A slurry of 5-hexyl-2-amino-1,3,4-thiadiazole (40 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-hexyl-1,3,4-thiadiazol-2-yl isocyanate dimer.

EXAMPLE 17

Preparation of the Dimethyl Acetal of 2-[1-Ethyl-3-(5-hexyl-1,3,4-thiadiazol-2-yl)ureido]-acetaldehyde A mixture of 5-hexyl-1,3,4-thiadiazol-2-yl isocyanate dimer (0.05 mole), the dimethyl acetal of 2-ethylaminoacetaldehyde (0.1 mole) and benzene (60 ml)

are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-ethyl-3-(5-hexyl-1,3,4-thiadiazol-2-yl)ureido]acetaldehyde.

EXAMPLE 18

Preparation of 1-(5-Hexyl-1,3,4-thiadiazol-2-yl)-3-ethyl-5-hydroxy-1,3-imidazolidin-2-one The dimethyl acetal of 2-[1-ethyl-3-(5-hexyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-hexyl-1,3,4-thiadiazol-2-yl)-3-ethyl-5-hydroxy-1,3-imidazolidin-2-one.

EXAMPLE 19

Preparation of 1-(5-Hexyl-1,3,4-thiadiazol-2-yl)-3-ethyl-5-allylamino-1,3-imidazolidin-2-one 1-(5-Hexyl-1,3,4-thiadiazol-2-yl)-3-ethyl-5-hydroxy-1,3-imidazolidin-2-one (0.1 mole), allyl amine (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stirred of solvent under reduced pressure to yield the desired product 1-(5-hexyl-1,3,4-thiadizol-2-yl)-3-ethyl-5-allylamino-1,3-imidazolidin-2-one as the residue.

EXAMPLE 20

Preparation of 5-Methoxy-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methoxy-2-amino-1,3,4-thiadiazole (40 grams) in ethyl acetate (300 ml) is added to the reaction vessel, and the resulting mixture is stirred for a period of about 16 hours, resulting in the formation of a precipitate. The reaction mixture is then purged with nitrogen as to remove unreacted phosgene. The purged mixture is then filtered to recover the precipitate. The precipitate is then recrystallized to yield the desired product 5-methoxy-1,3,4-thiadiazol-2-yl isocyanate dimer.

EXAMPLE 21

Preparation of the Dimethyl Acetal of 2-[1-Ethyl-3-(5-methoxy-1,3,4-thiadiazol-2-yl)ureido]acetaldehyde A mixture of 5-methoxy-1,3,4-thiadiazol-2-yl isocyanate dimer (0.05 mole), the dimethyl acetal of 2-ethylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-ethyl-3-(5-methoxy-1,3,4-thiadiazol-2-yl)ureido]acetaldehyde.

EXAMPLE 22

Preparation of 1-(5-Methoxy-1,3,4-thiadiazol-2-yl)-3-ethyl-5-hydroxy-1,3-imidazolidin-2one The dimethyl acetal of 2-[1-ethyl-3-(5-methoxy-1,3,4-thiadiazol-2-yl)-ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-methoxy-1,3,4-thiadiazol-2-yl)-3-ethyl-5-hydroxy-1,3-imidazolidin-2-one.

EXAMPLE 23

Preparation of 1-(5-Methoxy-1,3,4-thiadiazol-2yl)-3-ethyl-5-cyclopropylamino-1,3-imidazolidin-2-one 1-(5-Methoxy-1,3,4-thiadiazol-2-yl)-3ethyl-5-hydroxy-1,3-imidazolidin-2one (0.1 mole), cyclopropylamine (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-methoxy-1,3,4-thiadiazol-2-yl)-3-ethyl-5-cyclopropylamino-1,3-imidazolidin-2-one as the residue.

EXAMPLE 24

Prepaation of 5-Methylthio-1,3,4-thiadiazol-2-yl Ioscyanate Dimer

A saturated solution of phosgene in ethyl acetate (100 ml) is charged into a glass reaction vessel equipped with a mechanical stirrer. A slurry of 5-methylthio-2-amino-1,3,4-thiadiazole (45 grams) in ethyl acetate (300 ml) is added to the reaction vessel, and the resulting mixture is stirred for a period of about 16 hours, resulting in the formation of a precipitate. The reaction mixture is then purged with nitrogen gas to to remove unreacted phosgene. The purged mixture is filtered to recover the precipitate. The precipitate is then recrystallized to yield the desired product 5-methylthio-1,3,4-thiadiazol-2-yl isocyanate dimer.

EXAMPLE 25

Preparation of the Dimethyl Acetal of 2-[1-Propyl-3-(5-methylthio-1,3,4-thiadiazol-2-yl)ureido]acetaldehyde A mixture of 5-methylthio-1,3,4-thiadiazol-2-yl isocyanate dimer (0.05 mole), the dimethyl acetal of 2-propylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-propyl-3-(5-methylthio-1,3,4-thiadiazol-2-yl)ureido]acetaldehyde.

EXAMPLE 26
Preparation of 1(5-Methylthio-1,3,4-thiadiazol-2-yl)-3-propyl-5-hydroxy-1,3-imidazolidin-2-one The dimethyl acetal of 2-[1-propyl-3-(5-methylthio-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-methylthio-1,3,4-thiadiazol-2-yl)-3-propyl-5-hydroxy-1,3-imidazolidin-2-one.

EXAMPLE 27
Preparation of 1-(5-Methylthio-1,3,4-thiadiazol-2-yl)-3-propyl-5-γ-chloropropylamino-1,3-imidazolidin-2-one 1-(5-Methylthio-1,3,4-thiadiazol-2-yl)-3-propyl-5-hydroxy-1,3-imidazolidin-2-one (0.01 mole), γ-chloropropylamine (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-methylthio-1,3,4-thiadiazol-2-yl)-3-propyl-5-γ-chloropropylamino-1,3-imidazolidin-2-one as the residue.

EXAMPLE 28
Preparation of 5-Methylsulfonyl-1,3,4-thiadiazol-2-yl Isocyanate Dimer A saturated solution of phosgene in ethyl acetate (100 ml) is charged into a glass reaction vessel equipped with a mechanical stirrer. A slurry of 5-methylsulfonyl-2-amino-1,3,4-thiadiazole (50 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfonyl-1,3,4-thiadiazol-2-yl isocyanate dimer.

EXAMPLE 29
Preparation of the Dimethyl Acetal of 2-[1-Allyl-3-(5-methylsulfonyl-1,3,4-thiadiazol-2-yl)ureido]acetaldehyde A mixture of 5-methylsulfonyl-1,3,4-thiadiazol-2-yl isocyanate dimer (0.05 mole), the dimethyl acetal of 2-allylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-allyl-3-(5-methylsulfonyl-1,3,4-thiadiazol-2-yl)ureido]acetaldehyde.

EXAMPLE 30
Preparation of 1-(5-Methylsulfonyl-1,3,4-thiadiazol-2-yl)-3allyl-5-hydroxy-1,3-imidazolidin-2-one The dimethyl acetal of 2-[1-allyl-3-(5-methylsulfonyl-1,3,4-thiadiazol-2-yl)ureido]acetaldehyde (15 grams), water (400 ml) and hydrochloric acid (4 ml) are charged into a glass reaction vessel equipped with mechanical stirrer, thermometer and reflux condenser. The reaction mixture is heated are reflux for a period of about 15 minutes. The reaction mixture is then filtered while hot, and the filtrate is cooled to form a precipitate. The precipitate is recovered by filtration, is dried and is recrystallized to yield the desired product 1-(5-methylsulfonyl-1,3,4-thiadiazol-2-yl)-3-allyl-5-hydroxy-1,3-imidazolidin-2-one.

EXAMPLE 31
Preparation of 1-(5-Methylsulfonyl-1,3,4-thiadiazol-2-yl)-3-allyl-5-(N-methyl-N-cyclohexylamino)-1,3-imidazolidin-2-one 1-(5-Methylsulfonyl-1,3,4-thiadiazol-2-yl)-3-allyl-5-hydroxy-1,3-imidazolidin-2-one (0.1 mole), N-methyl-N-cyclohexylamine (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-methylsulfonyl-1,3,4-thiadiazol-2-yl)-3-allyl-5-(N-methyl-N-cyclohexylamino)-1,3-imidazolidin-2-one.

EXAMPLE 32
Preparation of 5-Methylsulfinyl-1,3,4-thiadiadiazol-2-yl Isocyanate Dimer A saturated solution of phosgene in ethyl acetate (100 ml) is charged into a glass reaction vessel equipped with a mechanical stirrer. A slurry of 5-methylsulfinyl-2-amino-1,3,4-thiadiazole (50 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfinyl-1,3,4-thiadiazol-2-yl isocyanate dimer.

EXAMPLE 33
Preparation of the Dimethyl Acetal of 2-[1-Methyl-3-(5-methylsulfinyl-1,3,4-thiadiazol-2-yl)ureido]acetaldehyde A mixture of 5-methylsulfinyl-1,3,4-thiadiazol-2-yl isocyanate dimer (0.05 mole), the dimethyl acetal of 2-methylaminoacetaldehyde (0.1 mole) and benzene (60 ml) are changed into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-methylsulfinyl-1,3,4-thiadiazol-2-yl)ureido]-acetaldehyde.

EXAMPLE 34

Preparation of 1-(5-Methylsulfinyl-1,3,4-thiadiazol-2-yl)-3-methyl-5-hydroxy-1,3-imidazolidin-2-one The dimethyl acetal of 2-[1-methyl-3-(5-methylsulfinyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-methylsulfinyl-1,3,4-thiadiazol-2-yl)-3-methyl-5-hydroxy-1,3-imidazolidin-2-one.

EXAMPLE 35

Preparation of 1-(5-Methylsulfinyl-1,3,4-thiadiazol-2-yl)-3-methyl-5-(2-methylanilino)-1,3-imidazolidin-2-one 1-(5-Methylsulfinyl-1,3,4-thiadiazol-2-yl)-3-methyl-5-hydroxy-1,3-imidazolidin-2-one (0.1 mole), 2-methylaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-methylsulfinyl-1,3,4-thiadiazol-2-yl)-3-methyl-5-(2-methylanilino)-1,3-imidazolidin-2-one as the residue.

EXAMPLE 36

Preparation of 5-Cyclopropyl-1,3,4-thiadiazol-2-yl Isocyanate Dimer

A satuated solution of phosgene in ethyl acetate (100 ml) was charged into a glass reaction vessel equipped with a mechanical stirrer. A slurry of 5-cyclopropyl-2-amino-1,3,4-thiadiazole (6 grams) in ethyl acetate (100 ml) was added to the reaction vessel, and the resulting mixture was stirred for a period of about 16 hours, resulting in the formation of a precipitate. The reaction mixture was then purged with nitrogen gas to remove unreacted phosgene. The purged mixture was filtered to recover the desired product 5-cyclopropyl-1,3,4-thiadiazol-2-yl isocyanate dimer.

EXAMPLE 37

Preparation of the Dimethyl Acetal of 2-[1-Propargyl-3-(5-cyclopropyl-1,3,4-thiadiazol-2-yl)ureido]acetaldehyde A mixture of 5-cyclopropyl-1,3,4-thiadiazol-2-yl isocyanate dimer (7 grams), the dimethyl acetate of 2-propargylaminoacetaldehyde (5 grams) and ethyl acetate (50 ml) were charged into a glass reaction vessel equipped with a mechanical stirrer and reflux condenser. The reaction mixture is heated at reflux for a period of about 2 hours. After this time the mixture is stripped of solvent under reduced pressure to yield the desired product the dimethyl acetal of 2-[1-propargyl-3-(5-cyclopropyl-1,3,4-thiadiazol-2-yl)ureido]acetaldehyde as an oil.

EXAMPLE 38

Preparation of 1-(5-Cyclopropyl-1,3,4-thiadiazol-2-yl)-3-propargyl-5-hydroxy-1,3-imidazolidin-2-one The dimethyl acetal of 2-[1-propargyl-3-(5-cyclopropyl-1,3,4-thiadiazol-2-yl)ureido]acetaldehyde obtained from Example 37, water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipiate. The precipitate is recovered by filtration, is dried and is recrystallized from ethyl acetate to yield the desired product 1-(5-cyclopropyl-1,3,4-thiadiazol-2-yl)-3-propargyl-5-hydroxy-1,3-imidazolidin-2-one.

EXAMPLE 39

Preparation of 1-(5-Cyclopropyl-1,3,4-thiadiazol-2-yl)-3-propargyl-5-(2-methoxyanilino)-1,3-imidazolidin-2-one 1-(5-Cyclopropyl-1,3,4-thiadiazol-2-yl)-3-propargyl-5-hydroxy-1,3-imidazolidin-2-one (0.1 mole), 2-methoxyaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1(5-cyclopropyl-1,3,4-thiadiazol-2-yl)-3-propargyl-5-(2-methoxyanilino-1,3-imidazolidin-2-one as the residue.

EXAMPLE 40

Preparation of 5-Cyclohexyl-1,3,4-thiadiazol-2-yl Isocyanate Dimer

A saturated solution of phosgene in ethyl acetae (500 ml) is charged into a glass reaction vessel equipped with a mechanical stirrer. 5-Cyclohexyl-2-amino-1,3,4-thiadiazole (6 grams) is added to the reaction vessel, and the resulting mixture is stirred and heated at reflux for a period of about 4 hours, resulting in the formation of a precipitate. The reaction mixture is then purged with nitrogen gas to remove unreacted phosgene. The purged mixture is then filtered to recover the precipitate. The precipitate is then recrystallized from a dimethyl formamide-water mixture to yield the desired product 5-cyclohexyl-1,3,4-thiadiazol-2-yl isocyanate dimer having a melting point of 237° to 239° C.

EXAMPLE 41

Preparation of the Dimethyl Acetal of 2-[1-Methyl-3-(5-cyclohexyl-1,3,4-thiadiazol-2-yl)ureido]acetaldehyde A mixture of 5-cyclohexyl-1,3,4-thiadiazol-2-yl isocyanate dimer (12 grams), the dimethyl acetal of 2-methylaminoacetaldehyde (6.9 grams) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized from methanol to yield the desired product the dimethyl acetal of 2-[1-methyl-3-(5-cyclohexyl-1,3,4-thiadiazol-2-yl)ureido]acetaldehyde having a melt point of 133° to 134° C.

EXAMPLE 42

Preparation of 1-(5-Cyclohexyl-1,3,4-thiadiazol-2-yl)-3-methyl-5-hydroxy-1,3-imidazolidin-2-one The dimethyl acetal of 2-[1-methyl-3-(5-cyclohexyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized from methanol to yield the desired product 1-(5-cyclohexyl-1,3,4-thiadiazol-2-yl)-3-methyl-5-hydroxy-1,3-imidazolidin-2-one having a melt point of 154° to 155° C.

EXAMPLE 43

Preparation of 1-(5-Cyclohexyl-1,3,4-thiadiazol-2-yl)-3-methyl-5-(3,4-dichloroanilino)-1,3-imidazolidin-2-one 1-(5-Cyclohexyl-1,3,4-thiadiazol-2-yl)-3-methyl-5-hydroxy-1,3-imidazolidin-2-one (0.1 mole), 3,4-dichloroaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-cyclohexyl-1,3,4-thiadiazol-2-yl)-3-methyl-5-(3,4-dichloroanilino)-1,3-imidazolidin-2-one as the residue.

EXAMPLE 44

Preparation of 5-Cyclopentyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-cyclopentyl-2-amino-1,3,4-thiadiazole (50 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-cyclopentyl-1,3,4-thiadiazol-2-yl isocyanate dimer.

EXAMPLE 45

Preparation of the Dimethyl Acetal of 2-[1-Methyl-3-(5-cyclopentyl-1,3,4-thiadiazol-2-yl)ureido]acetaldehyde A mixture of 5-cyclopentyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-cyclopentyl-1,3,4-thiadiazol-2-yl)ureido]acetaldehyde.

EXAMPLE 46

Preparation of 1-(5-Cyclopentyl-1,3,4-thiadiazol-2-yl)-3-methyl-5-hydroxy-1,3-imidazolidin-2-one The dimethyl acetal of 2-[1-methyl-3-(5-cyclopentyl-1,3,4-thiadiazol-1-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-cyclopentyl-1,3,4-thiadiazol-2-yl)-3-methyl-5-hydroxy-1,3-imidazolidin-2-one.

EXAMPLE 47

Preparation of 1-(5-Cyclopentyl-1,3,4-thiadiazol-2-yl)-3-methyl-5-(4-trifluoromethylanilino)-1,3-imidazolidin-2-one 1-(5-Cyclopentyl-1,3,4-thiadiazol-2-yl)-3-methyl-5-hydroxy-1,3-imidazolidin-2-one (0.1 mole), 4-trifluoromethylaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-cyclopentyl-1,3,4-thiadiazol-2-yl)-3-methyl-5-(4-trifluoromethylanilino)-1,3-imidazolidin-2-one as the residue.

EXAMPLE 48

Preparation of 1-(5-Trifluoromethyl-1,3,4-thiadiazol-2-yl)-3-methyl-5-β-methoxyethylamino-1,3-imidazolidin-2-one 1-(5-Trifluoromethyl-1,3,4-thiadiazol-2-yl)-3-methyl-5-hydroxy-1,3-imidazolidin-2-one (8.0 grams) and benzene (75 ml) were charged into a glass reaction vessel equipped with a mechanical stirrer, thermometer, Dean-Stark trap and reflux condenser. β-Methoxyethylamine (5.0 grams) was added to the reaction vessel, and the mixture was heated at reflux while removing the water as it was formed. After no more water was given off, the reaction mixture was cooled, resulting in the precipitation of a solid. This solid was recovered by filtration and was recrystallized from hexane to yield the desired product 1-(5-trifluoromethyl-1,3,4-thiadiazol-2-yl)-3-methyl-5-$\beta$-methoxyethylamino-1,3-imidazolidin-2-one having a melting point of 82° to 84° C.

EXAMPLE 49

Preparation of 5-Allyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-allyl-2-amino-1,3,4-thiadiazole (50 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-allyl-1,3,4-thiadiazol-2-yl isocyanate dimer.

EXAMPLE 50

Preparation of the Dimethyl Acetal of 2-[1-Methyl-3-(5-allyl-1,3,4-thiadiazol-2-yl)ureido]-acetaldehyde A mixture of 5-allyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-allyl-1,3,4-thiadiazol-2-yl)ureido]acetaldehyde.

EXAMPLE 51

Preparation of 1-(5-Allyl-1,3,4-thiadiazol-2-yl)-3-methyl-5-hydroxy-1,3-imidazolidin-2-one The dimethyl acetal of 2-[1-methyl-3-(5-allyl-1,3,4-thiadiazol-2-yl) ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-allyl-1,3,4-thiadiazol-2-yl)-3-methyl-5-hydroxy-1,3-imidazolidin-2-one.

EXAMPLE 52

Preparation of 1-(5-Allyl-1,3,4-thiadiazol-2-yl)-3-methyl-5-(3-nitroanilino)-1,3-imidazolidin-2-one 1-(5-Allyl-1,3,4-thiadiazol-2-yl)-3-methyl-5-hydroxy-1,3-imidazolidin-2-one (0.1 mole), 3-nitroaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stipped of solvent under reduced pressure to yield the desired product 1-(5-allyl-1,3,4-thiadiazol-2-yl)-3-methyl-5-(3-nitroanilino)-1,3-imidazolidin-2-one as the residue.

EXAMPLE 53

Preparation of 5-Pentyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-pentyl-2-amino-1,3,4-thiadiazole (40 grams) in ethyl acetate (300 ml) is added to the reaction vessel, and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-pentyl-1,3,4-thiadiazol-2-yl isocyanate dimer.

EXAMPLE 54

Preparation of the Dimethyl Acetal of 2-[1-Ethyl-3-5-pentyl-1,3,4-thiadiazol-2-yl)ureido]-acetaldehyde A mixture of 5-pentyl-1,3,4-thiadiazol-2-yl isocyanate dimer (0.05 mole), the dimethyl acetal of 2-ethylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-ethyl-3-(5-pentyl-1,3,4-thiadiazol-2-yl)ureido]acetaldehyde.

EXAMPLE 55

Preparation of 1-5-Pentyl-1,3,4-thiadiazol-2-yl)-3-ethyl-5-hydroxy-1,3-imidazolidin-2-one The dimethyl acetal of 2-[1-ethyl-3-(5-pentyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot, and the filtrate is cooled to form a precipitate. The precipitate is recovered by filtration, is dried and is recrystallized to yield the desired product 1-(5-pentyl-1,3,4-thiadiazol-2-yl)-3-ethyl-5-hydroxy-1,3-imidazolidin-2-one.

EXAMPLE 56

Preparation of 1-(5-Pentyl-1,3,4-thiadiazol-2-yl)-3-ethyl-5-[N-methyl-N-(3-bromobenzyl)amino]-1,3-imidazolidin-2-one 1-(5-Pentyl-1,3,4-thiadiazol-2-yl)-3-ethyl-5-hydroxy-1,3-imidazolidin-2-one (0.1 mole), N-methyl-N-(3-bromobenzyl)-amino (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-pentyl-1,3,4-thiadiazol-2-yl)-3-ethyl-5-[N-methyl-N-(3-bromobenzyl)amino]-1,3-imidazolidin-2-one as the residue.

EXAMPLE 57

Preparation of
1-(5Trifluoromethyl-1,3,4-thiadiazol-2-yl)-3-methyl-5-(4-cyanoanilino)-1,3-imidazolidin-2-one 1-(5-Trifluoromethyl-1,3,4-thiadiazol-2-yl)-3-methyl-5-hydroxy-1,3-imidazolidin-2-one (0.1 mole), 4-cyanoaniline (0.11 mole) and benzene (100 ml) are charged into a glass reaction vessel equipped with a mechanical stirrer, thermometer, reflux condenser and Dean-Stark trap. The reaction mixture is heated at reflux, and the water of reaction is removed as it is formed. After no more water is formed, the reaction mixture is stripped of solvent under reduced pressure to yield the desired product 1-(5-trifluoromethyl-1,3,4-thiadiazol-2-yl)-3-methyl-5-(4-cyanoanilino)-1,3-imidazolidin-2-one as the residue.

EXAMPLE 58

Preparation of
1-(5-Trifluoromethyl-1,3,4-thiadiazol-2-yl)-3-methyl-5-octylamino-1,3-imidazolidin-2-one 1-(5-Trifluoromethyl-1,3,4-thiadiazol-2-yl)-3-methyl-5-hydroxy-1,3-imidazolidin-2-one (13.1 grams) and heptane (100 ml) are charged into a glass rection vessel equipped with a mechanical stirrer, thermometer, Dean-Stark trap and reflux condenser. Octylamine (10.0 grams) is added to the reaction vessel, and the mixture is heated at reflux while moving the water as it is formed. After no more water is given off, the reaction mixture is stripped of solvent to yield the desired product 1-(5-trifluoromethyl-1,3,4-thiadiazol-2-yl)-3-methyl-5-octylamino-1,3-imidazolidin-2-one.

EXAMPLE 59

Preparation of
1-(5-Trifluoromethyl-1,3,4-thiadiazol-2-yl)-3-methyl-5-dodecylamino-1,3-imidazolidin-2-one 1-(5-Trifluoromethyl-1,3,4-thiadiazol-2-yl)-3- methyl-5-hydroxy-1,3-imidazolidin-2-one (13.1 grams) and heptane (100 ml) are charged into a glass reaction vessel equipped with a mechanical stirrer, thermometer, Dean-Stark trap and reflux condenser. Dodecylamine (14.0 grams) is added to the reaction vessel, and the mixture is heated at reflux while removing the water as it is formed. After no more water is given off, the reaction mixture is stripped of solvent to yield the desired product 1-(5-trifluoromethyl-1,3,4-thiadiazol-2-yl)-3-methyl-5-dodecylamino-1,3-imidazolidin-2-one.

EXAMPLE 60

Preparation of
1-(5-Trifluoromethyl-1,3,4-thiadiazol-2-yl)-3-methyl-5-octadecylamino-1,3-imidazolidin-2-one 1-(5-Trifluoromethyl-1,3,4-thiadiazol-2-yl)-3-methyl-5-hydroxyl-1,3-imidazolidin-2-one (13.1 grams) and heptane (100 ml) are charged into a glass reaction vessel equipped with a mechanical stirrer, thermometer, Dean-Stark trap and reflux condenser. Octadecylamine (20.0 grams) is added to the reaction vessel, and the mixture is heated at reflux while removing the water as it is formed. After no more water is given off, the reaction mixture is stripped of solvent to yield the desired product 1-(5-trifluoromethyl-1,3,4-thiadiazol-2-yl)-3-methyl-5-octadecylamino-1,3-imidazolidin-2-one.

EXAMPLE 61

Preparation of
1-(5-t-Butyl-1,3,4-thiadiazol-2-yl)-3-methyl-5-dodecylamino-1,3-imidazolidin-2-one 1-(5-t-Butyl-1,3,4-thiadiazol-2-yl)-3-methyl-5-hydroxy-1,3-imidazolidin-2-one (13.4 grams), dodecylamine (12.0 grams) and heptane (100 ml) are charged into a glass reaction vessel equipped with a mechanical stirrer, thermometer, reflux condenser and Dean-Stark trap. The reaction mixture is heated at reflux, and the water of reaction is removed as it is formed by azeotroping. After no more water is given off, the reaction mixture is stripped of solvent to yield the desired product 1-(5-t-butyl-1,3,4-thiadiazol-2-yl)-3-methyl-5-dodecylamino-1,3-imidazolidin-2-one.

EXAMPLE 62

Preparation of
1-(5-t-Butyl-1,3,4-thiadiazol-2-yl)-3-methyl-5-octadecylamino-1,3-imidazolidin-2-one 1-(5-t-Butyl-1,3,4-thiadiazol-2-yl)-3-methyl-5-hydroxy-1,3-imidazolidin-2-one (13.4 grams), octadecylamine (6.0 grams) and heptane (100 ml) are charged into a glass reaction vessel equipped with a mechanical stirrer, thermometer, reflux condenser and Dean-Stark trap. The reaction mixture is heated at refux, and the water of reaction is removed as it is formed by azeotroping. After no more water is given off, the reaction mixture is stirred of solvent to yield the desired product 1-(5-t-butyl-1,3,4-thiadiazol-2-yl)-3-methyl-5-octadecylamino-1,3-imidazolidin-2-one.

Additional compounds within the scope of the present invention which can be prepared according to the procedures detailed in the foregoing examples are 1-(5-trifluoromethyl-1,3,4-thiadiazol-2-yl)-3-methyl-5-amino-1,3-imidazolidin-2-one, 1-(5-t-butyl-1,3,4-thiadiazol-2-yl)-3-methyl-5-amino-1,3-imidazolidin-2-one, 1-(5-trifluoromethyl-1,3,4-thiadiazol-2-yl)-3-ethyl-5-propylamino-1,3-imidazolidin-2-one, 1-(5-methyl-1,3,4-thiadiazol-2-yl)-3-butyl-5-(N,N-dimethylamino)-1,3-imidazolidin-2-one, 1-(5-ethyl-1,3,4-thiadiazol-2-yl)-3-pentyl-5-(N,N-dipropylamino)-1,3-imidazolidin-2-one, 1-(5-isopropyl-1,3,4-thiadiazol-2-yl)-3-hexyl-5-(N,N-dihexylamino)-1,3-imidazolidin-2-one, 1-(5-pentyl-1,3,4-thiadiazol-2-yl)-3-but-3-enyl-5-(N-methyl-N-butylamino)-1,3-imidazolidin-2-one, 1-(5-hexyl-1,3,4-thiadiazol-2-yl)-3-pent-4-enyl-5-(N-ethyl-N-phenylamino)-1,3-imidazolidin-2-one, 1-(5-cyclobutyl-1,3,4-thiadiazol-2-yl)-3-hex-4-enyl-5-(N-ethyl-N-benzylamino)-1,3-imidazolidin-2-one, 1-(5-cyclopentyl-1,3,4-thiadiazol-2-yl)-3-$\beta$-chloroethyl-5-(N-methyl-N-but-3-enylamino)-1,3-imidazolidin-2-one, 1-(5-cycloheptyl-1,3,4-thiadiazol-2-yl)-3-$\beta$-bromoethyl-5-hex-4-enylamino-1,3-imidazolidin-2-one, 1-(5-but-3-enyl-1,3,4-thiadiazol-2-yl)-3-$\gamma$-chloropropyl-5-$\beta$-ethoxyethylamino-1,3-imidazolidin-2-one, 1-(5-pent-4-enyl-1,3,4-thiadiazol-2-yl)-3-$\delta$-chlorohexyl-5-$\gamma$-ethoxypropylamino-1,3-imidazolidin-2-one, 1-(5-hex-4-enyl-1,3,4-thiadiazol-2-yl)-3-ethyl-5-$\delta$-propoxybutylamino-1,3-imidazolidin-2-one, 1-(5-$\beta$-bromoethyl-1,3,4- thiadiazol-2-yl)-3-methyl-5-ω-methoxyhexylamino-1,3-imidazolidin-2-one, 1-(5-γ-chloropropyl-1,3,4-thiadiazol-2-yl)-3-methyl-5-cyclobutylamino-1,3-imidazolidin-2-one, 1-(5-δ-chlorobutyl-1,3,4-thiadiazol-2-yl)-3-methyl-5-cyclopentylamino-1,3-imidazolidin-2-one, 1-(5-β-bromohexyl-1,3,4-thiadiazol-2-yl)-3-methyl-5-cyclohexylamino-1,3-imidazolidin-2-one, 1-(5-ethoxy-1,3,4-thiadiazol-2-yl)-3-methyl-5-cycloheptylamino-1,3-imidazolidin-2-one, 1-(5-butoxy-1,3,4-thiadiazol-2-yl)-3-methyl-5-β-hydroxyethylamino-1,3-imidazolidin-2-one, 1-(5-hexyloxy-1,3,4-thiadiazol-2-yl)-3-methyl-5-γ-hydroxypropylamino-1,3-imidazolidin-2-one 1-(5-ethylthio-1,3,4-thiadiazol-2-yl)-3-methyl-5-β-hydroxyhexylamino-1,3-imidazolidin-2-one, 1-(5-propylthio-1,3,4-thiadiazol-2-yl)-3-methyl-5-(2-ethylanilino)-1,3-imidazolidin-2-one, 1-(5-hexylthio-1,3,4-thiadiazol-2-yl)-3-methyl-5-(2-propylanilino)-1,3-imidazolidin-2-one, 1-(5-ethylsulfonyl-1,3,4-thiadiazol-2-yl)-3-methyl-5-(4-hexylanilino)-1,3-imidazolidin-2-one, 1-(5-butylsulfonyl-1,3,4-thiadiazol-2-yl)-3-methyl-5-(4-ethoxyanilino)-1,3-imidazolidin-2-one, 1-(5-hexylsulfonyl-1,3,4-thiadiazol-2-yl)-3-methyl-5-(4-hexyloxyanilino)-1,3-imidazolidin-2-one, 1-(5-ethylsulfinyl-1,3,4-thiadiazol-2-yl)-3-methyl-5-(4-iodoanilino)-1,3-imidazolidin-2-one, 1-(5-propylsulfinyl-1,3,4-thiadiazol-2-yl)-3-methyl-5-(4-fluoroanilino)-1,3-imidazolidin-2-one, 1-(5-hexylsulfinyl-1,3,4-thiadiazol-2-yl)-3-methyl-5-(3,4-dibromoanilino)-1,3-imidazolidin-2-one, 1-(5-t-butyl-1,3,4-thiadiazol-2-yl)-3-methyl-5-(3,4,5-trichloroanilino)-1,3-imidazolidin-2-one, 1-(5-trifluoromethyl-1,3,4-thiadiazol-2-yl)-3-methyl-5-(3-chloromethylanilino)-1,3-imidazolidin-2-one, 1-(5-t-butyl-1,3,4-thiadiazol-2-yl)-3-methyl-5-(3-β-chloroethylanilino)-1,3-imidazolidin-2-one, 1-(5-trifluoromethyl-1,3,4-thiadiazol-2-yl)-3-methyl-5-(4-ω-chlorohexylanilino)-1,3-imidazolidin-2-one, 1-(5-t-butyl-1,3,4-thiadiazol-2-yl)-3-methyl-5-(2-ethylthioanilino)-1,3-imidazolidin-2-one, 1-(5-trifluoromethyl-1,3,4-thiadiazol-2-yl)-3-methyl-5-(3-propylthioanilino)-1,3-imidazolidin-2-one, 1-(5-t-butyl-1,3,4-thiadiazol-2-yl)-3-methyl-5-(4-butylthioanilino)-1,3-imidazolidin-2-one, 1-(5-trifluoromethyl-1,3,4-thiadiazol-2-yl)-3-methyl-5-(3-hexylthioanilino)-1,3-imidazolidin-2-one, 1-(5-t-butyl-1,3,4-thiadiazol-2-yl)-3-methyl-5-[N-(2-methyl-4-chlorobenzyl)-amino]-1,3-imidazolidin-2-one, 1-(5-trifluoromethyl-1,3,4-thiadiazol-2-yl)-3-methyl-5-[N-ethyl-N-(2,6-dimethylbenzyl)-amino]-1,3-imidazolidin-2-one, 1-(5-t-butyl-1,3,4-thiadiazol-2-yl)-3-methyl-5-heptylamino-1,3-imidazolidin-2-one, 1-(5-t-butyl-1,3,4-thiadiazol-2-yl)-3-methyl-5-octylamino-1,3-imidazolidin-2-one, 1-(5-t-butyl-1,3,4-thiadiazol-2-yl)-3-methyl-5-nonylamino-1,3-imidazolidin-2-one, 1-(5-t-butyl-1,3,4-thiadiazol-2-yl)-3-methyl-5-decylamino-1,3-imidazolidin-2-one, 1-(5-t-butyl-1,3,4-thiadiazol-2-yl)-3-methyl-5-undecylamino-1,3-imidazolidin-2-one, 1-(5-t-butyl-1,3,4-thiadiazol-2-yl)-3-methyl-5-tridecylamino-1,3-imidazolidin-2-one, 1-(5-t-butyl-1,3,4-thiadiazol-2-yl)-3-methyl-5-tetradecylamino-1,3-imidazolidin-2-one, 1-(5-t-butyl-1,3,4-thiadiazol-2-yl)-3-methyl-5-pentadecylamino-1,3-imidazolidin-2-one, 1-(5-t-butyl-1,3,4-thiadiazol-2-yl)-3-methyl-5-hexadecylamino-1,3-imidazolidin-2-one, 1-(5-t-butyl-1,3,4-thiadiazol-2-yl)-3-methyl-5-heptadecylamino-1,3-imidazolidin-2-one and the like.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 63

Preparation of a Dust

| Product of Example 4 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal composition. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like, carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenyl-acetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroerephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lampsquarters, foxtail, crabgrass, wild mustard, field pennycress, ryegrass, goose grass, chickweed, wild oats, velvet-leaf, purslane, barnyardgrass, smartweed, knotweed, cocklebur, wild buckwheat, kochia, medic, corn cockle, ragweed, sow-thistle, coffeeweed, croton, cuphea, dodder, fumitory, groundsel, hemp nettle, knawel, spurge, spurry, emex, jungle rice, pondweed, dog fennel, carpetweed, morningglory, bed-straw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, round-leaved marrlow, bull thistle, hounds-tongue, moth mullein and purple star thistle; or perennials such as white cockle, perennial ryegrass, quackgrass, Johnsongrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small platic greenhouse pots filled with dry soil were seeded with the various weed seeds. Twenty-four hours or less after seeding the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of 21 days, at which time the condition of the plants and the degree of injury to the plants was rated on a scale of from 0 to 10, as follows: 0 = no injury, 1,2

= slight injury, 3,4 = moderate injury, 5,6 = moderately severe injury, 7,8,9 = severe injury and 10 = death. The effectiveness of these compounds is demonstrated by the data in Table I.

TABLE I

| Test Compound | Rate (lbs/acre) | YNSG | WOAT | JMWD | VTLF | JNGS | PIGW | WMSTD |
|---|---|---|---|---|---|---|---|---|
| Product of Example 4 | 8 | 5 | 10 | 10 | 10 | 9 | 10 | 10 |
| | 4 | 5 | 10 | 10 | 10 | 9 | 10 | 10 |
| | 2 | 3 | 10 | 10 | 10 | 10 | 10 | 10 |
| | 1 | 4 | 10 | 10 | 10 | 10 | 10 | 10 |
| | 1/2 | — | 10 | 9 | 10 | 10 | 10 | 10 |
| | 1/4 | — | 10 | 9 | 10 | 10 | 10 | 10 |
| | 1/8 | — | 9 | 9 | 10 | 10 | 10 | 10 |
| | 1/16 | — | 8 | 9 | 10 | 5 | 10 | 10 |
| Product of Example 8 | 8 | 5 | 10 | 10 | 10 | 5 | 10 | 10 |
| | 4 | 5 | 10 | 10 | 10 | 8 | 10 | 10 |
| | 2 | 5 | 10 | 10 | 10 | 8 | 10 | 10 |
| | 1 | 5 | 10 | 5 | 10 | 9 | 10 | 10 |
| | 1/4 | 3 | 10 | 8 | 10 | 9 | 10 | 10 |
| | 1/8 | 0 | 10 | 7 | 10 | 9 | 10 | 10 |
| | 1/16 | 0 | 6 | 3 | 10 | 7 | 10 | 10 |
| | 1/32 | 0 | 2 | 2 | 10 | 0 | 4 | 5 |
| Product of Example 9 | 8 | 4 | 10 | 6 | 10 | 10 | 10 | 10 |
| | 4 | 5 | 10 | 5 | 10 | 8 | 10 | 9 |
| | 2 | 5 | 10 | 10 | 10 | 10 | 10 | 10 |
| | 1 | 4 | 10 | 10 | 10 | 10 | 10 | 10 |
| | 1/2 | — | 10 | 8 | 10 | 10 | 10 | 10 |
| | 1/4 | — | 10 | 6 | 10 | 8 | 10 | 10 |
| | 1/8 | — | 10 | 7 | 10 | 7 | 10 | 10 |
| | 1/16 | — | 5 | 8 | 10 | 0 | 5 | 10 |

| Test Compound | Rate (lbs/acre) | YLFX | BNGS | CBGS | CTGS | MNGY | BDWD | SPGT | QKGS |
|---|---|---|---|---|---|---|---|---|---|
| Product of Example 4 | 8 | 9 | 10 | 9 | 10 | 10 | — | — | — |
| | 4 | 9 | 10 | 9 | 10 | 10 | — | — | — |
| | 2 | 9 | 10 | 9 | 10 | 10 | — | — | — |
| | 1 | 9 | 10 | 4 | 10 | 10 | — | — | — |
| | 1/2 | 9 | 10 | 0 | 10 | 10 | 10 | 10 | 10 |
| | 1/4 | 9 | 10 | 0 | 10 | 10 | 6 | 6 | 10 |
| | 1/8 | 6 | 8 | 0 | 4 | 10 | 3 | 3 | 10 |
| | 1/16 | 0 | 3 | 0 | 0 | 10 | 0 | 0 | 9 |
| Product of Example 8 | 8 | 10 | 10 | 10 | 10 | 8 | — | — | — |
| | 4 | 10 | 10 | 10 | 10 | 10 | — | — | — |
| | 2 | 9 | 10 | 8 | 10 | 10 | — | — | — |
| | 1 | 10 | 10 | 9 | 10 | 10 | — | — | — |
| | 1/4 | 10 | 10 | 9 | 10 | 10 | 10 | 10 | — |
| | 1/8 | 6 | 10 | 7 | 6 | 10 | 10 | 10 | — |
| | 1/16 | 4 | 8 | 0 | 0 | 6 | 4 | 0 | — |
| | 1/32 | 0 | 0 | 0 | 0 | 5 | 0 | 0 | — |
| Product of Example 9 | 8 | 7 | 10 | 9 | 10 | 10 | — | — | — |
| | 4 | 9 | 10 | 9 | 10 | 10 | — | — | — |
| | 2 | 8 | 10 | 8 | 10 | 10 | — | — | — |
| | 1 | 10 | 10 | 4 | 10 | 10 | — | — | — |
| | 1/2 | 10 | 10 | 6 | 10 | 10 | 10 | 10 | 10 |
| | 1/4 | 9 | 10 | 3 | 10 | 10 | 0 | 4 | 10 |
| | 1/8 | 9 | 10 | 2 | 9 | 10 | 0 | 4 | 10 |
| | 1/16 | 0 | 8 | 0 | 0 | 5 | 0 | 2 | 5 |

| Test Compound | Rate (lbs/acre) | YNSG | WOAT | JMWD | VTLF | JNGS | PIGW | WMSTD |
|---|---|---|---|---|---|---|---|---|
| Product of Example 11 | 1/2 | — | 10 | 10 | 10 | 9 | 10 | 10 |
| | 1/4 | — | 10 | 10 | 10 | 9 | 10 | 10 |
| | 1/8 | — | 9 | 7 | 10 | 8 | 10 | 10 |
| | 1/16 | — | 9 | 6 | 10 | 3 | 10 | 10 |
| Product of Example 12 | 1/2 | — | 10 | 6 | 10 | 9 | 10 | 10 |
| | 1/4 | — | 10 | 7 | 10 | 9 | 10 | 10 |
| | 1/8 | — | 10 | 5 | 10 | 7 | 10 | 10 |
| | 1/16 | — | 9 | 3 | 9 | 0 | 10 | 10 |
| Product of Example 14 | 1/4 | 0 | 10 | 6 | 10 | 9 | 10 | 10 |
| | 1/8 | 0 | 9 | 10 | 10 | 9 | 10 | 10 |
| | 1/16 | 0 | 10 | 7 | 10 | 8 | 10 | 10 |
| | 1/32 | 0 | 4 | 5 | 4 | 3 | 10 | 7 |
| Product of Example 15 | 1/2 | — | 10 | 7 | 10 | 9 | 10 | 10 |
| | 1/4 | — | 9 | 8 | 10 | 9 | 10 | 10 |
| | 1/8 | — | 6 | 5 | 10 | 6 | 10 | 10 |
| | 1/16 | — | 6 | 4 | 10 | 3 | 10 | 10 |
| Product of Example 48 | 1/2 | — | 10 | 8 | 8 | 9 | 10 | 10 |
| | 1/4 | — | 10 | 8 | 7 | 9 | 10 | 10 |
| | 1/8 | — | 10 | 7 | 8 | 6 | 10 | 10 |
| | 1/16 | — | 9 | 5 | 8 | 4 | 10 | 10 |

| Test Compound | Rate (lbs/acre) | YLFX | BNGS | CGBS | CTGS | MNGY | BDWD | SPGT | QKGS |
|---|---|---|---|---|---|---|---|---|---|
| Product of Example 11 | 1/2 | 9 | 10 | 4 | 10 | 10 | 10 | 10 | 9 |
| | 1/4 | 9 | 10 | 3 | 10 | 10 | 8 | 8 | 10 |
| | 1/8 | 9 | 9 | 0 | 10 | 10 | 3 | 5 | 10 |
| | 1/16 | 7 | 9 | 0 | 3 | 10 | 3 | 4 | 10 |
| Product of Example 12 | 1/2 | 9 | 10 | 5 | 10 | 10 | 10 | 10 | 10 |
| | 1/4 | 9 | 10 | 4 | 10 | 10 | 9 | 10 | 10 |
| | 1/8 | 9 | 10 | 3 | 10 | 10 | 3 | 4 | 10 |

TABLE I-continued

|  | 1/16 | 5 | 0 | 6 | 0 | 10 | 0 | 0 | 3 |
|---|---|---|---|---|---|---|---|---|---|
| Product of | 1/4 | 9 | 10 | 9 | 10 | 10 | 9 | 10 | — |
| Example 14 | 1/8 | 8 | 10 | 7 | 10 | 10 | 8 | 10 | — |
|  | 1/16 | 9 | 10 | 6 | 10 | 10 | 7 | 10 | — |
|  | 1/32 | 4 | 3 | 4 | 6 | 10 | 0 | 0 | — |
| Product of | 1/2 | 8 | 10 | 4 | 10 | 10 | 10 | 10 | 10 |
| Example 15 | 1/4 | 9 | 10 | 0 | 9 | 10 | 10 | 7 | 10 |
|  | 1/8 | 9 | 9 | 0 | 10 | 10 | 4 | 7 | 5 |
|  | 1/16 | 4 | 4 | 0 | 3 | 10 | 3 | 0 | 3 |
| Product of | 1/2 | 9 | 10 | 4 | 10 | 10 | 9 | 10 | 10 |
| Example 48 | 1/4 | 9 | 10 | 4 | 10 | 10 | 4 | 9 | 10 |
|  | 1/8 | 9 | 10 | 3 | 7 | 10 | 0 | 7 | 10 |
|  | 1/16 | 9 | 7 | 2 | 6 | 10 | 0 | 3 | 7 |

YNSG = Yellow Nutsedge  
WOAT = Wild Oats  
JMWD = Jimsonweed  
VTLF = Velvetleaf  
JNGS = Johnsongrass  
PIGW = Pigweed  
WMSTD = Wild Mustard  
YLFX = Yellow Foxtail  
BNGS = Barnyardgrass  
CBGS = Crabgrass  
CTGS = Cheatgrass  
MNGY = Wild Morningglory  
BDWD = Bindweed  
SPGT = Sprangletop  
QKGS = Quackgrass The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the weeds that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretofore described. The effectiveness of these compounds is demonstrated by the data in Tables II and III.

TABLE II

| Test Compound | Rate (lbs/A) | Weed Species | | | | | | |
|---|---|---|---|---|---|---|---|---|
|  |  | YNSG | WOAT | PIGW | JNGS | BDWD | WMSTD | YLFX |
| Product of | 1/2 | — | 10 | 10 | 10 | 10 | 10 | 10 |
| Example 4 | 1/4 | — | 9 | 10 | 10 | 10 | 10 | 10 |
|  | 1/8 | — | 6 | 10 | 7 | 6 | 10 | 7 |
|  | 1/16 | — | 0 | 10 | 6 | 3 | 10 | 0 |
| Product of | 8 | 10 | 10 | 10 | 10 | 10 | 10 | 10 |
| Example 8 | 4 | 9 | 10 | 10 | 10 | 10 | 10 | 10 |
|  | 2 | 10 | 10 | 10 | 10 | 10 | 10 | 10 |
|  | 1 | 10 | 10 | 10 | 9 | 10 | 10 | 9 |
|  | 1/2 | — | 10 | 10 | 8 | 9 | 10 | 10 |
|  | 1/4 | 0 | 10* | 10* | 9* | 10* | 10* | 10* |
|  | 1/8 | 0 | 8.5* | 10* | 7.5* | 5.5* | 10* | 8.5* |
|  | 1/16 | 0 | 5.5* | 10* | 4.5* | 4.5* | 10* | 4.5* |
|  | 1/32 | 0 | 0 | 3 | 4 | 0 | 4 | 0 |
| Product of | 8 | 6 | 10 | 10 | 10 | 10 | 10 | 10 |
| Example 9 | 4 | 8 | 10 | 10 | 10 | 10 | 10 | 10 |
|  | 2 | 8 | 10 | 10 | 10 | 10 | 10 | 10 |
|  | 1 | 5 | 10 | 10 | 10 | 10 | 10 | 10 |
|  | 1/2 | — | 10* | 10* | 9.5* | 10* | 10* | 10* |
|  | 1/4 | — | 10* | 10* | 9.5* | 8* | 10* | 10* |
|  | 1/8 | — | 7.5* | 10* | 8.5* | 10* | 10* | 9* |
|  | 1/16 | — | 4* | 10* | 3* | 8* | 10* | 4* |
| Product of | 1/2 | — | 9 | 10 | 10 | 6 | 10 | 10 |
| Exammple 11 | 1/4 | — | 9 | 10 | 10 | 7 | 10 | 9 |
|  | 1/8 | — | 3 | 10 | 3 | 4 | 10 | 0 |
|  | 1/16 | — | 3 | 10 | 4 | 0 | 10 | 0 |

| Test Compound | Rate (lbs/A) | Weed Species | | | | | | |
|---|---|---|---|---|---|---|---|---|
|  |  | BNGS | CBGS | MNGY | JMWD | SPGT | CTGS | VTLF |
| Product of | 1/2 | 9 | 4 | 10 | 10 | 10 | 10 | 10 |
| Example 4 | 1/4 | 9 | 3 | 10 | 10 | 7 | 10 | 10 |
|  | 1/8 | 9 | 2 | 10 | 10 | 4 | 7 | 8 |
|  | 1/16 | 0 | 0 | 10 | 10 | 3 | 0 | 7 |
| Product of | 8 | 10 | 10 | 10 | 10 | — | — | — |
| Example 8 | 4 | 10 | 10 | 10 | 10 | — | — | — |
|  | 2 | 10 | 10 | 10 | 10 | — | — | — |
|  | 1 | 10 | 10 | 10 | 10 | — | — | — |
|  | 1/2 | 10 | — | 10 | 10 | — | — | 10 |
|  | 1/4 | 10* | 8 | 10* | 10* | 10 | 10 | 10* |
|  | 1/8 | 10* | 9 | 10* | 6.5* | 9 | 7 | 10* |
|  | 1/16 | 6.5* | 0 | 9* | 5* | 5 | 0 | 10* |
|  | 1/32 | 4 | 0 | 4 | 3 | 3 | 0 | 3 |
| Product of | 8 | 10 | 10 | 10 | 10 | — | — | — |
| Example 9 | 4 | 10 | 10 | 9 | 10 | — | — | — |
|  | 2 | 10 | 9 | 10 | 10 | — | — | — |
|  | 1 | 10 | 9 | 9 | 10 | — | — | — |
|  | 1/2 | 10* | 10 | 9* | 10* | 10 | 10 | 10* |
|  | 1/4 | 9.5* | 8 | 10* | 10* | 10 | 10 | 10* |
|  | 1/8 | 8* | 5 | 10* | 10* | 10 | 10 | 10* |
|  | 1/16 | 3.5* | 2 | 10* | 10* | 3 | 3 | 5* |
| Product of | 1/2 | 9 | 4 | 10 | 10 | 8 | 10 | 9 |
| Example 11 | 1/4 | 9 | 3 | 10 | 9 | 5 | 7 | 10 |
|  | 1/8 | 7 | 0 | 10 | 9 | 7 | 2 | 9 |
|  | 1/16 | 0 | 0 | 9 | 10 | 3 | 3 | 4 |

| Test Compound | Rate (lbs/A) | Weed Species | | | | | | |
|---|---|---|---|---|---|---|---|---|
|  |  | YNSG | WOAT | PIGW | JNGS | BDWD | WMSTD | YLFX |

TABLE II-continued

| Test Compound | Rate (lbs/A) | | | | | | | |
|---|---|---|---|---|---|---|---|---|
| Product of Example 12 | 1/2 | — | 9 | 10 | 10 | 10 | 10 | 10 |
| | 1/4 | — | 10 | 10 | 10 | 10 | 10 | 10 |
| | 1/8 | — | 9 | 10 | 3 | 10 | 10 | 9 |
| | 1/16 | — | 3 | 10 | 4 | 10 | 10 | 3 |
| Product of Example 14 | 1/4 | 3 | 10 | 10 | 9 | 10 | 10 | 10 |
| | 1/8 | 0 | 10 | 10 | 9 | 9 | 10 | 8 |
| | 1/16 | 0 | 4 | 5 | 8 | 5 | 10 | 0 |
| | 1/32 | 0 | 0 | 2 | 5 | 0 | 5 | 0 |
| Product of Example 15 | 1/2 | — | 10 | 10 | 10 | 10 | 10 | 10 |
| | 1/4 | — | 9 | 10 | 10 | 10 | 10 | 10 |
| | 1/8 | — | 5 | 10 | 4 | 10 | 10 | 3 |
| | 1/16 | — | 3 | 10 | 4 | 10 | 10 | 3 |
| Product of Example 48 | 1/2 | — | 10 | 10 | 10 | 9 | 10 | 10 |
| | 1/4* | — | 9 | 10 | 10 | 8 | 10 | 8 |
| | 1/8 | — | 10 | 10 | 7 | 6 | 10 | 9 |
| | 1/16 | — | 0 | 10 | 8 | 3 | 10 | 7 |

| Test Compound | Rate (lbs/A) | Weed Species | | | | | | |
|---|---|---|---|---|---|---|---|---|
| | | BNGS | CBGS | MNGY | JMWD | SGT | CTGS | VTLF |
| Product of Example 12 | 1/2 | 9 | 7 | 10 | 10 | 10 | 10 | 6 |
| | 1/4 | 9 | 6 | 10 | 10 | 3 | 10 | 5 |
| | 1/8 | 7 | 0 | 10 | 10 | 3 | 9 | 6 |
| | 1/16 | 5 | 0 | 10 | 9 | 3 | 6 | 5 |
| Product of Example 14 | 1/4 | 10 | 10 | 10 | 10 | 10 | 10 | 10 |
| | 1/8 | 10 | 5 | 10 | 6 | 3 | 4 | 10 |
| | 1/16 | 7 | 0 | 6 | 8 | 5 | 0 | 10 |
| | 1/32 | 0 | 0 | 4 | 0 | 0 | 0 | 10 |
| Product of Example 15 | 1/2 | 9 | 2 | 10 | 10 | 10 | 10 | 10 |
| | 1/4 | 9 | 2 | 10 | 10 | 9 | 10 | 7 |
| | 1/8 | 7 | 0 | 10 | 8 | 2 | 7 | 6 |
| | 1/16 | 3 | 0 | 8 | 10 | 0 | 3 | 6 |
| Product of Example 48 | 1/2 | 9 | 5 | 10 | 10 | 10 | 10 | 10 |
| | 1/4 | 9 | 5 | 10 | 10 | 10 | 10 | 10 |
| | 1/8 | 7 | 4 | 10 | 10 | 2 | 10 | 10 |
| | 1/16 | 3 | 0 | 10 | 7 | 4 | 7 | 10 |

YNSG = Yellow Nutsedge  WMSTD = Wild Mustard  MNGY = Morningglory
WOAT = Wild Oats  YLFX = Yellow Foxtail  JMWD = Jimsonweed
PIGW = Pigweed  BNGS = Barnyardgrass  SPGT = Sprangletop
INGS = Johnsongrass  CBGS = Crabgrass  CTGS = Cheatgrass
BDWD = Bindweed  VTLF = Velvetleaf

*Ratings are averages of two tests.

TABLE III

| Test Compound | Rate (lbs/A) | Weed Species | | | | | | |
|---|---|---|---|---|---|---|---|---|
| | | GTFX | FXMT | WTRGS | LMQR | TFES | QKGS | A BLUE |
| Product of Example 8 | 1/2 | 10 | 10 | 10 | 10 | 10 | 10 | 10 |
| | 1/4 | 10 | 10 | 10 | 10 | 10 | 10 | 10 |
| | 1/8 | 10 | 8 | 10 | 10 | 9 | 7 | 10 |
| | 1/16 | 5 | 3 | 5 | 9 | 0 | 7 | 10 |
| Product of Example 9 | 1/2 | 10 | 10 | 10 | 9 | 10 | 10 | 10 |
| | 1/4 | 10 | 10 | 10 | 9 | 10 | 10 | 10 |
| | 1/8 | 10 | 10 | 10 | 9 | 10 | 10 | 10 |
| | 1/16 | 10 | 10 | 7 | 9 | 6 | 7 | 10 |

GTFX = Giant Foxtail  LMQR = Lambsquarter
FXMT = Foxtail Millet  TFES = Tall Fescue
WTRGS = Watergrass  QKGS = Quackgrass
A BLUE = Annual Bluegrass

I claim:
1. A Compound of the formula

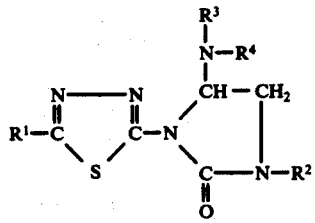

wherein $R^1$ is selected from the group consisting of alkyl of up to 18 carbon atoms, cycloalkyl of from 3 to 7 carbon atoms, lower alkenyl, lower chloroalkyl, lower bromoalkyl, trifluoromethyl, lower alkoxy, lower alkylthio, lower alkylsulfonyl and lower alkylsulfinyl; $R^2$ is selected from the group consisting of lower alkyl, lower alkenyl, lower haloalkyl and propargyl and $R^3$ and $R^4$ are each selected from the group consisting of hydrogen, lower alkyl, lower alkenyl, lower haloalkyl, lower hydroxyalkyl, lower alkoxyalkyl, cycloalkyl of from 3 to 7 carbon atoms and

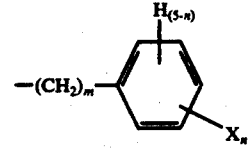

wherein X is selected from the group consisting of lower alkyl, lower alkoxy, halogen, lower haloalkyl, lower alkylthio, nitro and cyano; $n$ is an integer from 0 to 3; and $m$ is the integer 0 or 1, provided that a maximum of one of $R^3$ and $R^4$ is an aromatic moiety.

2. The compound of claim 1, 1-(5-trifluoromethyl-1,3,4-thiadiazol-2-yl)-3-methyl-5-t-butylamino-1,3-imidazolidin-2-one.

3. The compound of claim 1, 1-(5-t-butyl-1,3,4-thiadiazol-2-yl)-3-methyl-5-hexylamino-1,3-imidazolidin-2-one.

4. The compound of claim 1, 1-(5-trifluoromethyl-1,3,4-thiadiazol-2-yl)-3-methyl-5-hexylamino-1,3-imidazolidin-2-one.

5. The compound of claim 1, 1-(5-trifluoromethyl-1,3,4-thiadiazol-2-yl)-3-methyl-5-anilino-1,3-imidazolidin-2-one.

6. The compound of claim 1, 1-(5-trifluoromethyl-1,3,4-thiadiazol-2-yl)-3-methyl-5-benzylamino-1,3-imidazolidin-2-one.

7. The compound of claim 1, 1-(5-trifluoromethyl-1,3,4-thiadiazol-2-yl)-3-methyl-5-$\beta$-hydroxyethylamino-1,3-imidazolidin-2-one.

8. The compound of claim 1, 1-(5-trifluoromethyl-1,3,4-thiadiazol-2-yl)-3-methyl-5-diethylamino-1,3-imidazolidin-2-one.

9. A herbicidal composition comprising an inert carrier and, as an essential active ingredient, in a quantity toxic to weeds, a compound of claim 1.

10. A method of controlling weeds which comprises contacting said weeds with a herbicidal composition comprising an inert carrier and, as an essential active ingredient, in a quentity toxic to weeds, a compound of claim 1.

* * * * *